United States Patent [19]

Ruse

[11] Patent Number: 4,879,245
[45] Date of Patent: Nov. 7, 1989

[54] MEASURING THE CONCENTRATION OF TWO COMPONENTS IN A GAS BLEND

[75] Inventor: Alois Ruse, Oberursel, Fed. Rep. of Germany

[73] Assignee: Hartmann & Braun AG, Frankfurt am Main, Fed. Rep. of Germany

[21] Appl. No.: 762,714

[22] Filed: Aug. 5, 1985

[30] Foreign Application Priority Data

Aug. 4, 1984 [DE] Fed. Rep. of Germany ....... 3428814
Sep. 4, 1984 [DE] Fed. Rep. of Germany ....... 3432444

[51] Int. Cl.$^4$ .............................................. G01N 33/00
[52] U.S. Cl. .................................. 436/124; 436/121; 436/122; 436/144; 436/181; 422/83; 422/93
[58] Field of Search ............... 436/124, 144, 181, 164, 436/121, 122; 422/83, 93

[56] References Cited

U.S. PATENT DOCUMENTS 3,486,861 12/1969 Wiseman ........................ 436/144 X

FOREIGN PATENT DOCUMENTS 0040922 3/1980 Japan .

Primary Examiner—Barry S. Richman
Assistant Examiner—Lynn M. Kummert
Attorney, Agent, or Firm—Ralf H. Siegemund

[57] ABSTRACT

A single gas analyzer is used for analyzing the concentration of two gaseous components such as hydrogen and chlorine in a blend by responding to the chlorine content in the gas blend there being a UV-type reactor for the formation of hydrochloric acid and the operation is such that the gas to be analyzed alternates between a path in which the reaction has taken place and one in which such a reaction has not taken place, for directly measuring the concentration of the gas with a higher concentration and indirectly the concentration of the gas with the lower concentration by determining the depletion the reaction has caused in the higher concentration gas.

3 Claims, 1 Drawing Sheet

MEASURING THE CONCENTRATION OF TWO COMPONENTS IN A GAS BLEND

BACKGROUND OF THE INVENTION

The present invention relates to the ascertaining and determination of the concentration of two components of a blend or mixture of gas such as chlorine and hydrogen gas.

The components of the type referred to above can be determined by means of two analyzers each responding to one of the components. It is possible, however, to use a single analyzer which then will have to be adjusted accordingly. The known equipment, however, is therefore rather complicated and extensive.

DESCRIPTION OF THE INVENTION

It is an object of the present invention to provide a new and improved method for determining and measuring the concentration of two components in a gas blend which components may react with each other.

In accordance with the preferred embodiment of the present invention it is suggested to measure first the concentration of a component whose concentration is expected to be the larger value and by means of a single analyzer; that particular measuring result (value A) is then stored as a suitable measured quantity. Next both components are caused to react for purposes of generating a new compound and that portion of the larger concentration component which did not react with the other one is then measured again through the same analyzer which of course still responds to that particular kind of component one; the result of this measurement (value B) is stored in the second store and the two values A and B are then, for example, fed to a computer or an algebraic circuit network ascertaining the difference (A−B) of the measuring values which difference in fact is representative of or proportional (stoichiometric relation) to the component of smaller concentration which has been chemically bound to a portion of the larger concentration component. The difference of the values A and B will be equal to the component of smaller concentration if the gas volume is not changed by the reaction but that may not be true in some instances, on the other hand such a volume change is a known parameter and can readily be introduced in the evaluation of the measuring result.

It can thus be seen that the measurement carried out in accordance with the invention uses an analyzer responding to one particular component and the measuring result may be simultaneously indicated in an appropriate instrument such that the measurement is carried out on a quasi-continuous basis, one merely alternates cyclically between the ascertainment of value A and value B, one indicating the undepleted concentration of the large concentration component, the other one the partially depleted concentration. By way of example one may have the two components chlorine and hydrogen in a gas blend and the measurement carried out in accordance with the invention is well suited for determining the relative proportion of these components. For example the possibility exists to determine the content of hydrogen in moist chlorine in a quantitative basis under simultaneous analysis of the presence of chlorine.

In accordance with the method of the invention one uses an analyzer which responds specifically to the presence of chlorine and the measuring value above is then indicative of the chlorine content. Subsequently the gas blend undergoes reaction, e.g. through operation of a valve or turning on of a reaction initiator (e.g. a UV-source) so that hydrochloric acid is generated out of the hydrogen and chlorine gases. Thus, one either alternates between bypass and insertion of the reactor, or the reactor is continuously flown through by the chlorine and hydrogen towards the analyzer but the reaction between the components by applying ultraviolet radiation is intermittently interrupted by turning off the effectiveness of that source. In either case the portion of the chlorine which is not bound in the HCl acid is subsequently fed into the analyzer and a second measuring value, the value B, is determined whereupon the difference between the beginning and the final chlorine content is ascertained by the formation of the value (A−B) and as stated the difference is an indication for the concentration of hydrogen in the blend.

DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

Proceeding now to the detailed description of the drawings it should be mentioned that the two devices shown in the two figures both are provided for analyzing a gas blend in the sense that the chlorine and hydrogen content in that blend is to be ascertained. It is assumed that there is a relatively high proportion of chlorine in the blend such that the formation of HCl acid under utilization of all of the hydrogen in the blend will not use up all of the chlorine.

Figure 1:
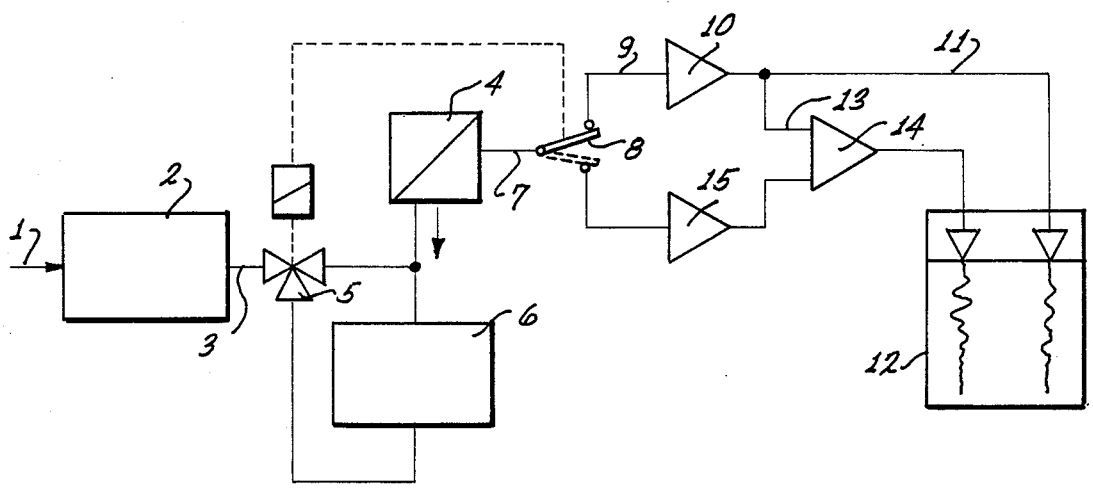
FIG. 1 is a block diagram of a first example for practicing the preferred embodiment of the present invention in accordance with the best mode thereof.

Turning specifically to FIG. 1 a gas blend of the type to be analyzed is fed via a conduit 1 to a preparatory stage 2 serving as temporary buffer or being used to heat or cool the gas as it may be required or the like. Following these preparatory proceedings in device 2 the gas is fed via a conduit 3 to the analyzer 4 which is per se of known construction and designed to indicate immediately and directly the content of chlorine gas that it receives. A preferably magnetically operated valve 5 is arranged in the conduit 3 so as to include selectively a reactor 6 in the flow path that reaches the analyzer 4. Thus it can be seen that the analyzer 4 can be made to receive alternatingly gas in its original consistency as well as gas that has been subjected to a certain reaction.

For purposes of measurement the output of the analyzer 4 is supplied to an electrical conductor 7. In case the valve 5 has a position in which the reactor 6 is bypassed the measured value in line 7 will be indicative of the relative content of chlorine in the gas blend. If the switch or valve 5 is placed in the alternative position the analyzer 4 measures the chlorine that is not consumed after the reaction has taken place in the reaction device 6. The first mentioned measured value, value A when present in line 7 is fed via a switch in the illustrated position to an input line 9 for signal storage device 10. The storage device 10 can also be described as equivalent to a sample-and-hold circuit and provides its output signal (measuring value A) to a line 11 for direct indication by an instrument 12 being a plotter. In addition storage device and hold circuit 10 provide its signal to line 13 being one input of a differential amplifier 14. The output of that amplifier 14 is fed as second indicator to the instrument 12.

Switch 8 is operated in synchronism with a magnetic valve 5. Thus, as the reactor 6 is inserted in the gas input path for the analyzer 4 switch 8 changes position and feeds the output of line 7 to another store and sample-and-hold circuit 15. Electronic switches, relays or the like can be used for this purpose particularly as configuration of the switch 8. Following the changeover of valve 5 and switch 8 the two components $H_2$ and $C_{12}$ are fed to the reactor 6 wherein the hydrogen under the effect of ultraviolet radiation combines with the chlorine to HCl following the equation $H_2 + C_{12} = 2HCl$. All of the hydrogen will be used up in this reaction, but since it is assumed that stoichiometrically more chlorine is contained in the mixture some chlorine will be left over. The gas blend leaving the reactor 6 is fed to the analyzer 4 which now responds to the reduced chlorine content and furnishes measuring value B. Owing to the changeover of the switch 8 this measured value is fed to the sample-and-hold circuit 15 which in turn feeds its output as second input to the differential amplifier 14. Whence the algebraic computing element 14 forms the difference A−B which is directly representative of the content of hydrogen in the original blend. As stated this output value of the differential amplifier 14 is fed as second input to the indicator 12. Thus a running indication is provided for the hydrogen and chlorine content in the gas blend. It can thus be seen that for example processes in which chlorine is processed can very easily be monitored including for example chlorine liquification or chlorine alkali electrolysis.

Figure 2:
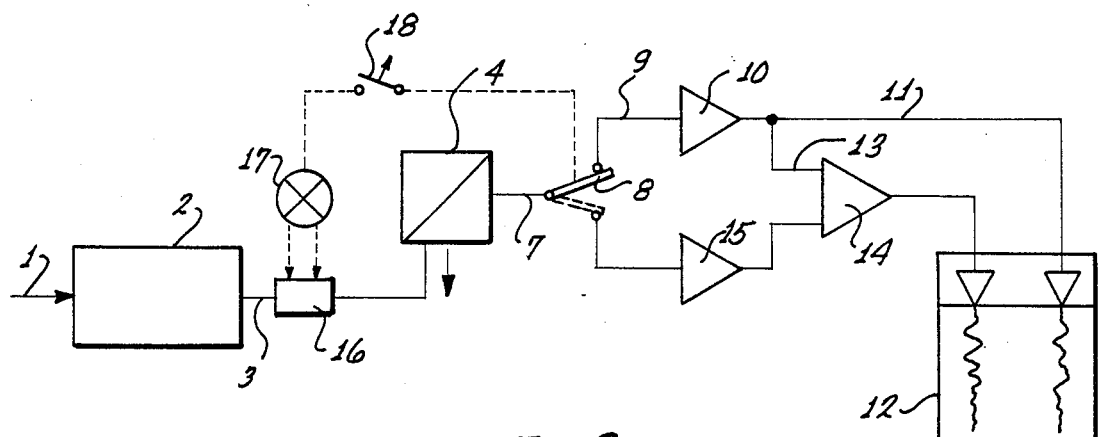
FIG. 2 is a similar block diagram of a modified equipment still practicing the best mode of the invention in accordance with the preferred embodiment.

Proceeding now to the description of the device shown in FIG. 2 this particular arrangement is constructed so that a bypass or the reaction is not needed. In both figures similar reference numerals are used to indicate corresponding parts. Thus in this case there is also a conduit 1, a preparatory stage 2 for the gas blend that arrives through the conduit 1 and after suitable preparation the gas is fed via a line 3 but now always through a reactor 16 to reach the analyzer 4 providing an indication of the chlorine content of whatever gas is received. Elements 7, 8, 9, 10, 11, 12, 13, 14 and 15 are all similar to parts used under like designation with reference to FIG. 1.

The reactor 16 operates under utilization of an ultraviolet radiation source 17 to cause the hydrogen to combine with the stoichiometrically requisite portion of chlorine. The operation is intermittently interrupted in that the radiation source 17 is alternatingly turned on and off by means of a switch 18 which of course is synchronized with the operation of the switch 8.

It can thus be seen that as long as the source 17 is turned off, switch 18 being open and switch 8 having again the illustrated position, no reaction takes place in the reactor 16 so that unmodified gas reaches the analyzer 4 measuring the chlorine content, measuring value A. The processing of that measuring value is the same as outlined above with reference to FIG. 1. Subsequently switch 8 changes position and switch 18 is closed. As switch 18 closes the ultraviolet source 17 is turned on and hydrogen reacts with chlorine in the reactor 16 so that the gas blend loses its hydrogen content due to the formation of hydrochloric acid. The analyzer then ascertains the reduced chlorine content, measuring value B, just as was already outlined with reference to FIG. 1.

The invention is not limited to the embodiments described above but all changes and modifications thereof, not constituting departures from the spirit and scope of the invention, are intended to be included.

I claim:

1. Method for ascertaining the concentration of two components in a gaseous blend, wherein the gases are amenable for reacting with each other, comprising the steps of:

using a single analyzer and a reaction chamber in an input path for the analyzer and bypassing that reaction chamber for alternatingly ascertaining a depleted and an undepleted concentration of the component with the larger concentration;

measuring the concentration of that one of the two components expected to have a larger concentration, by means of said single analyzer, including as substeps bypassing the reaction chamber and storing temporarily a measured value as measured by the analyzer when bypassing the reaction chamber, and indicating a representation of that measured value;

causing the two components to react to form a new compound such that one of the two components having a smaller concentration, is completely used up by the reaction to obtain said depleted concentration;

measuring a residual concentration of the first, mentioned larger concentration component following the reaction in the reaction chamber to thereby ascertain that portion of that larger concentration component not used up by the reaction, and storing separately a resulting measuring value; and forming the difference between the two measured values as indication and representation of the component with the smaller concentration.

2. Method for ascertaining the concentration of two components in a gaseous blend, wherein the gases are amenable for reacting with each other, comprising the steps of:

causing the two components to react in a reaction chamber to form a new compound such that that one of the two components having a smaller concentration, is completely used up by the reaction;

measuring the concentration of that one of the two components expected to have a larger concentration, by means of a single analyzer;

feeding the gas to be analyzed to the analyzer via said reaction chamber and alternatingly operating the reaction chamber so as to obtain and not to obtain the reaction, to thereby alternatingly generate measurement values for the depleted and undepleted concentration of the component with the larger concentration; storing temporarily a measured value as measured by the analyzer when the reaction chamber is not operated for the reactor, and indicating a representation of that measured value;

measuring a residual concentration of the first, mentioned larger concentration component following the reaction to thereby ascertain that portion of that larger concentration component not used up by the reaction, and storing separately a resulting measuring value; and forming the difference between the two measured values as indication and representation of the component with the smaller concentration.

3. Method for ascertaining the concentration of two components in a gaseous blend, wherein the gases are amenable for reacting with each other, comprising the steps of:

causing the two components to react in a reaction chamber to form a new compound such that that one of the two components having a smaller concentration, is completely used up by the reaction;

measuring the concentration of that one of the two components expected to have a larger concentration, by means of a single analyzer with a single output; alternatingly feeding to the analyzer the gas blend which has not been depleted of the compound with the larger concentration and a gas blend that has been depleted of the portion of the component with the larger concentration on account of the reaction;

storing temporarily a measured value as measured by the analyzer when there was no depletion and indicating a representation of that measured value;

measuring a residual concentration of the first, mentioned larger concentration component following the reaction to thereby ascertain that portion of that larger concentration component not used up by the reaction, and storing separately a resulting measuring value; and further including the steps of alternatingly sampling and holding the respective measured values and providing a difference value between them and concurrently indicating the difference as indication and respresentation of the component with the smaller concentration and the measured value corresponding to the undepleted concentration of the component with the larger concentration.

* * * * *